US006407136B1

(12) United States Patent
Scott et al.

(10) Patent No.: US 6,407,136 B1
(45) Date of Patent: Jun. 18, 2002

(54) 1,4-DITHIIN AND 1,4-DITHIEPIN-1,1,4,4, TETROXIDE DERIVATIVES USEFUL AS ANTAGONISTS OF THE HUMAN GALANIN RECEPTOR

(75) Inventors: Malcolm K. Scott, Lansdale; Daniel H. S. Lee, Northampton; Allen B. Reitz, Lansdale; Tina Morgan Ross, Audubon; Haou-Yan Wang, Philadelphia, all of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/563,147

(22) Filed: May 2, 2000

Related U.S. Application Data

(60) Provisional application No. 60/135,418, filed on May 21, 1999.

(51) Int. Cl.[7] .................... A61K 31/385; A61K 31/38; C07D 339/00; C07D 409/00
(52) U.S. Cl. .................... 514/436; 514/431; 549/11; 549/21
(58) Field of Search .................... 549/11, 21; 514/431, 514/436

(56) References Cited

U.S. PATENT DOCUMENTS

| | | |
|---|---|---|
| 3,920,438 A | 11/1975 | Brewer et al. |
| 3,997,323 A | 12/1976 | Brewer et al. |
| 4,004,018 A | 1/1977 | Brewer et al. |
| 4,026,906 A | 5/1977 | Brewer et al. |
| 4,094,988 A | 6/1978 | Johnson |
| 4,097,580 A | 6/1978 | Brewer et al. |

FOREIGN PATENT DOCUMENTS

EP    0 514 361    5/1992

OTHER PUBLICATIONS

Johnson et al, "1,4–Dithiin Oxides", Chem. Abs. 90:87477, 1979.*
Wang et al., "Galanin Receptor Subtypes as Potential Therapeutic Targets" Ex. Opin. Ther. Patents, vol., 8, No. 10, 1998 pp. 1225–1235.
Pooga M. et al., "Novel Galanin Receptor Ligands" Journal of Peptide Research, Copenhagen, vol. 51, No. 1, 1998, pp. 65–74.
Jozsef Jeko et al., gem–Difluorination vs 1,3–Dithiolane–Dihydro–1,4–dithiin Rearrangement The Role of Benzylic Carbons, *J. Org. Chem.* 1991, pp. 6748–6751.
Romualdo Caputo et al., Reactivity of Ethanediyl S,S–Acetals; 2. Synthesis of 2,3–Dihydro–1,4–dithiins, Synthesis Mar. 1991, 223–224.
A. Polak and M. Tisler, Synthesis of Pyridazine Derivatives–III Formation of Some Bicyclic Heterocyclic Systems, Tetrahedron 1965, vol. 21, 1323–1326.
Carlos A.M. Afonso et al., Synthesis of 2,3–Dihydro–1, 4–dithiins and 2–Alkylidene–1,4–dithianes by 1,2–Sulfur Migration in 2–(1–Hydroxyalkyl)–1,3–dithiolanes, Synthesis Jul. 1991, pp. 575–580.

* cited by examiner

*Primary Examiner*—Deborah C. Lambkin
(74) *Attorney, Agent, or Firm*—Mary Appollina

(57) ABSTRACT

The invention is directed to 1,4-dithiin- and 1,4-dithiepin-1,1,4,4-tetroxide derivatives useful as galanin receptor antagonists for treating disorders of the central nervous system. Pharmaceutical compositions comprising the compounds of the present invention and methods of treating conditions such as an eating disorder, obesity, bulimia nervosa, anorexia nervosa, binge eating, diabetes, dyslipidemia, hypertension, memory loss, sleep disturbances, pain, depression, anxiety, Alzheimer's disease, senile dementia, cerebral hemorrhage, or diarrhea are also described.

25 Claims, No Drawings

1,4-DITHIIN AND 1,4-DITHIEPIN-1,1,4,4, TETROXIDE DERIVATIVES USEFUL AS ANTAGONISTS OF THE HUMAN GALANIN RECEPTOR

CROSS-REFERENCE TO RELATED APPLICATION

This application claims priority from U.S. provisional application Ser. No. 60/135,418, filed May 21, 1999, the contents of which are hereby incorporated by reference.

FIELD OF THE INVENTION

This invention relates to a series of 1,4-dithiin- and 1,4-dithiepin-1,1,4,4-tetroxide derivatives and their use for the treatment of central nervous system disorders and affective conditions. More particularly, the compounds of the invention are ligands for the human galanin receptor.

BACKGROUND OF THE INVENTION

The galanin neuropeptide is a 29–30 amino acid peptide that is found in mammalian central (CNS) and peripheral (PVS) nervous systems (Bartfai, T.; Hokfelt, T.; Langel, U., Galanin-A Neuroendocrine Peptide. *Crit. Rev. Neurobiol.,* 1993, 7, 229–274; Crawley, J. N., Biological Actions of Galanin, *Regulatory Neuropeptides,* 1995, 59, 1–16; Kask, K.; Berthold, M.; Bartfai, T., Galanin Receptors: Involvement in Feeding, Pain, Depression, and Alzheimer's Disease. *Life Sci.,* 1997, 60,1523–1533). In the CNS, galanin is distributed in axons and neurons located in the thalamus, hypothalamus, cortex, amygdala, hippocampus and spinal cord (Melander, T.; Hokfelt, T.; Rokaeus, A., Distribution of Galanin-like Immunoreactivity in the Rat Central Nervous System. *J. Comp. Neurol,* 1986, 248, 475–517; Skofitsch, G.; Jacobowitz, D. M., Immunohistochemical Mapping of Galanin-like Neurons in the Rat Central Nervous System. *Peptides,* 1985, 6, 509–516), while in the PVS, it is found in pancreas, gastrointestinal, bladder, and genital tissue (Rokaeus, A., Galanin: A Newly Isolated Biologically Active Peptide. *Trends Neurosci.,* 1987, 10, 158–164).

The effects of galanin in mammalian CNS are due to its interaction with at least three galanin receptors, GalR1, GalR2, and GalR3 which have been isolated, characterized, and cloned (Wang, S., Parker, E. M., Galanin Receptor Subtypes as Potential Therapeutic Targets. *Exp. Opin. Ther. Patents,* 1998, 8, 1225–1335 and references therein). While GalR1 is predominately found in the CNS, GalR2 and GalR3 are also present in small amounts.

The galanin-1 (GALR-1), galanin-2 (GALR-2) and galanin-3 (GALR-3) receptors are G protein-coupled 7-transmembrane domain receptors which are negatively coupled to cyclic AMP. GALR-1, GALR-2 and GALR-3 are receptors found in rats, monkeys and humans.

The various effects exerted by the galanin neuropeptide include stimulated feeding in rats (Crawley, J. N., Galanin Antagonists Block Galanin-Induced Feeding in the Hypothalamus and Amygdala of the Rat. *Eur. J. Neurosci.,* 1993, 5, 1528–1533), enhanced firing of noradrenergic neurons and suppression of serotonin metabolism in rat brain raphe nucleus and locus coeruleus resulting in depressive behavior (Bartfai, T., Langel, U., Galanin Receptor Ligands as Potential Therapeutic Agents in Depression and Neurodegeneration *Eur. J. Med. Che.* 1995, 30, 163–174), impairment of cognitive performance in rats (Crawley, J. N., Wenk, G. L., Co-existence of Galanin and Acetylcholine: Is Galanin Involved in Memory Processes and Dementia? *Trends Neurosci.* 1989, 12, 278–282), inhibition of dopaminergic cell bodies in the ventral tegmentum resulting in depressive behavior (Weiss, J. M.; Bonsall, R. W.; Demetrikopoulos, M. K.; Emery, M. S.; West, C. H. K., Galanin: A Significant Role in Depression? *Ann. N. Y. Acad. Sci.,* 1998, 863, 364–382.), inhibition of acetylcholine release in rat hippocampus resulting in loss of cognition and learning (Chan-Palay, V. L., Galanin Hyperinnervates Surviving Neurons of the Human Basal Nucleus of Meynert in Dementias of Alzheimer's and Parkinson's Disease: A Hypothesis for the Role of Galanin in Accentuating Cholinergic Function in Dementia. 1988 *J. Comp. Neurol.* 273, 543–557; Crawley, J. N., Wenk, G. L., Co-existence of Galanin and Acetylcholine: Is Galanin Involved in Memory Processes and Dementia? *Trends Neurosci.* 1989, 12, 278–282; Crawley, J. N., Functional Interactions of Galanin and Acetylcholine: Relevance to Memory and Alzheimer's Disease *Behav. Brain Res.,* 1993, 57,133–141), and potentiation of the spinal analgesic effect of morphine or cholecysokinnin-B antagonists (Wiesenfeld-Hallin, Z., Xu, X. J., Langel, U., Bedecs, K., Hokfelt, T., Bartfai, T., Galanin-Mediated Control of Pain: Enhanced Role After Nerve Injury. *Pro. Natl. Acad. Sci. USA,* 1992, 89, 3334–3337.)

Thus a selective antagonist for the galanin receptor, specifically the human GALR (hGALR), may be useful in ameliorating diseases and conditions resulting from the binding of GAL to the hGALR, for example feeding disorders and diseases and conditions arising therein, depression and its attending disorders, or cognitive disorders such as Alzheimer's disease or senile dementia.

Compounds of the general structure of 1,4-dithiin-1,1,4,4-tetroxide derivatives are known in the literature as antimicrobial agents [U.S. Pat. No. 4,097,580, issued Jun. 27, 1978 (A. D. Brewer and R. A. Davis), U.S. Pat. No. 4,094,988, issued Jun. 13, 1978 (R. C. Johnson) and U.S. Pat. No. 4,004,018, issued Jan. 18, 1977 (A. D. Brewer and R. A. Davis) ] and plant growth regulants and herbicides [U.S. Pat. No. 4,026,906, issued May 31, 1977 (A. D. Brewer, R. W. Niedermyer, W. S. McIntire), U.S. Pat. No. 3,920,438, issued Nov. 18, 1975 (A. D. Brewer, R. W. Niedermyer, W. S. McIntire) and U.S. Pat. No. 3,997,323, issued Dec. 14, 1976 (A. D. Brewer, R. W. Niedermyer, W. S. McIntire)].

It is an object of the invention to identify compounds that bind to hGALR. It is another object of the invention to identify compounds which act as antagonist of the hGALR. Still another object of the invention is to identify compounds which are useful for treating conditions and/or disorders mediated by the hGALR. Another object of the invention is to identify compounds which are useful for treating conditions and/or disorders such as eating disorder, obesity, bulimia nervosa, anorexia nervosa, binge eating, diabetes, dyslipidimia, hypertension, memory loss, sleep disturbances, pain, depression, anxiety, Alzheimer's disease, senile dementia, cerebral hemorrhage, or diarrhea.

It has now been found that the 1,4-dithiin- and 1,4-dithiepin-1,1,4,4-tetroxide compounds of the present invention are antagonists for the hGAL receptor. As antagonists of the hGAL receptor, the compounds of the present invention inhibit the GAL-induced inhibition of acetylcholine release in rat hippocampal brain slices. Thus, the compounds of the present invention are useful for treating conditions and/or disorders mediated by the hGALR such as eating disorder, obesity, bulimia nervosa, anorexia nervosa, binge eating, diabetes, dyslipidimia, hypertension, memory loss, sleep disturbances, pain, depression, anxiety, Alzheimer's disease, senile dementia, cerebral hemorrhage, or diarrhea.

SUMMARY OF THE INVENTION

The present invention is direct to compounds of the formulas (I) and (II):

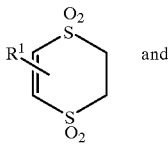

and

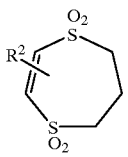

preferably of the formulas:

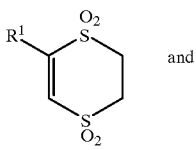

and

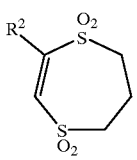

wherein $R^1$ is selected from the group consisting of ar$C_1$–$C_8$ alkyl, substituted ar$C_1$–$C_8$ alkyl where the substituent is $NR^3R^4$, $C_1$–$C_8$ alkyl, unsubstituted or substituted aryl, and unsubstituted or substituted heteroaryl, where the substituents on the aryl or heteroaryl are independently selected from one or more of halogen, $C_1$–$C_8$ alkyl, $C_3$–$C_8$ cycloalkyl, $C_1$–$C_8$, alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or ar$C_1$–$C_8$ alkylamido;

$R^2$ is selected from the group consisting of $C_1$–$C_8$ alkyl, unsubstituted or substituted ar$C_1$–$C_8$alkyl, unsubstituted or substituted aryl, and unsubstituted or substituted heteroaryl, where the substituents on the aryl or heteroaryl are independently selected from one or more of halogen, $C_1$–$C_8$ alkyl, $C_3$–$C_8$ cycloalkyl, $C_1$–$C_8$ alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or ar$C_1$–$C_8$ alkylamido;

$R^3$ and $R^4$ are independently selected from hydrogen, $C_1$–$C_8$ alkyl, benzoyl or substituted benzoyl where the substituent is $C_1$–$C_8$ alkoxy;

and pharmaceutically acceptable salts thereof.

In one embodiment of the invention are compounds of the formula (I) wherein $R^1$ is selected from the group consisting of substituted ar$C_1$–$C_8$ alkyl where the substituent is $NR^3R^4$; where $R^3$ and $R^4$ are independently selected from hydrogen, $C_1$–$C_8$ alkyl, benzoyl or substituted benzoyl, where the substituent on the benzoyl is $C_1$–$C_8$ alkoxy; and pharmaceutically acceptable salts thereof. Preferably, $R^1$ is substituted phenyl$C_1$–$C_4$ alkyl where the substitution is $NR^3N^4$; most preferably $R^1$ is 1-amino-2-phenylethyl or 1-[[4-butoxy]benzamido]-2-phenylethyl; and pharmaceutically acceptable salts thereof.

In another embodiment of the invention are compounds of the formula (II) wherein $R^2$ is selected from the group consisting of $C_1$–$C_8$ alkyl, unsubstituted or substituted aryl, and unsubstituted or substituted heteroaryl, where the substituents on the aryl or heteroaryl are independently selected from one or more of halogen, $C_1$–$C_8$ alkyl, $C_3$–$C_8$ cycloalkyl, $C_1$–$C_8$ alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or ar$C_1$–$C_8$ alkylamido; provided that when $R^2$ is poly-substituted phenyl, the substituents are independently selected from two or more of halogen, $C_1$–$C_8$ alkyl, $C_3$–$C_8$ cycloalkyl, $C_2$–$C_8$ alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or ar$C_1$–$C_8$ alkylamido; and pharmaceutically acceptable salts thereof.

In a class of the invention are compounds of the formula (II) wherein $R^2$ is selected from the group consisting of thienyl, naphthyl, phenyl and mono-substituted phenyl wherein the substituent on the phenyl is selected from halogen, $C_1$–$C_6$ alkyl, $C_1$–$C_6$ cycloalkyl, $C_1$–$C_6$ alkoxy, trifluoromethyl, trifluoromethoxy, phenyloxy $C_1$–$C_6$ alkylamido, phenyl, carboxy, $C_1$–$C_4$ alkoxycarbonyl, phenyloxycarbonyl, phenylsulfonyl, or phenyl$C_1$–$C_4$ alkylamido;

and pharmaceutically acceptable salts thereof.

In a subclass of the invention are compounds of the formula (II) wherein $R^2$ is selected from 2-thienyl, 3-thienyl, phenyl, 1-naphthyl, or mono-substituted phenyl wherein the substituent is selected from the group consisting of 4-methyl, 4-ethyl, 4-ethoxy, 2-fluoro, 4-fluoro, 4-bromo, 4-phenoxy, 4-trifluoromethoxy, and 3-phenyloxycarbonyl; and pharmaceutically acceptable salts thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. A further illustration of the invention is a process for making a pharmaceutical composition comprising mixing any of the compounds described above and a pharmaceutically acceptable carrier.

Included in the invention is the use of any of the compounds described above for the preparation of a medicament for treating a disorder mediated by a human galanin receptor, preferably, a human galanin-1 receptor, in a subject in need thereof.

Also included in the invention is the use of any of the compounds described above for the preparation of a medicament for treating a condition selected from eating disorder, obesity, bulimia nervosa, anorexia nervosa, binge eating, diabetes, dyslipidimia, hypertension, memory loss, sleep disturbances, pain, depression, anxiety, Alzheimer's disease, senile dementia, cerebral hemorrhage, or diarrhea in a subject in need thereof.

Exemplifying the invention are methods of treating a disorder mediated by a human galanin receptor, preferably, a human galanin-1 receptor, in a subject in need thereof, comprising administering to the subject a therapeutically effective amount of any of the compounds or pharmaceutical compositions described above.

An example of the invention is a method for treating a condition selected from eating disorder, obesity, bulimia nervosa, anorexia nervosa, binge eating, diabetes, dyslipidimia, hypertension, memory loss, sleep disturbances, pain, depression, anxiety, Alzheimer's disease, senile dementia, cerebral hemorrhage, or diarrhea in a subject in need thereof, comprising administering to the subject an effective amount of any of the compounds or pharmaceutical compositions described above.

In another aspect of the invention is a high throughput screening method for identifying compounds which bind to a human galanin-1 receptor on Bowes melanoma cells comprising the steps of:

(a) coupling a radiolabeled human galanin-1 receptor (preferably, $^{125}$I human galanin-1 receptor) to SPA beads;

(b) adding radiolabeled human galanin (preferably, $^{125}$I human galanin) to the coupled SPA beads from step a;

(c) adding a test compound to the mixture from step b; and (d) measuring the ability of the test compound to inhibit $^{125}$I human galanin binding to the coupled SPA beads.

DETAILED DESCRIPTION OF THE INVENTION

The present invention provides 1,4-dithiin- and 1,4 dithiepin-1,1,4,4-tetroxide derivative compounds, useful as ligands of the human galanin receptor, specifically the human galanin-1, human galanin-2 and human galanin-3 receptors. More particularly, the present invention is directed to 1,4-dithiin-1,1,4,4-tetroxide derivatives and 1,4,-dithiepin-1,1,4,4-tetroxide derivatives of the formulas (I) and (II):

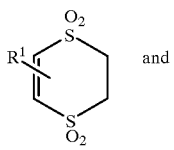
(I)

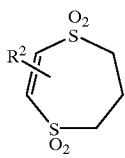
(II)

and pharmaceutically acceptable salts thereof, wherein $R^1$ and $R^2$ are as previously defined.

Preferably, the compound has the formula

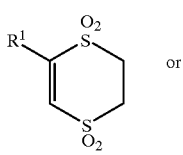
(I)

or

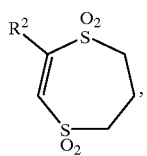
(II)

most preferably,

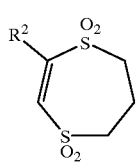
(II)

The compounds of the present invention may also be present in the form of pharmaceutically acceptable salts. For use in medicine, the salts of the compounds of this invention refer to non-toxic "pharmaceutically acceptable salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, unless otherwise noted, the term "halogen" shall include chlorine, fluorine, bromine and iodine.

As used herein, unless otherwise noted, the terms "alkyl" and "alkoxy" whether used alone or as part of a substituent group, include straight and branched chains having 1–8 carbon atoms, or any number within this range. For example, alkyl radicals include methyl, ethyl, n-propyl, isopropyl, n-butyl, isobutyl, sec-butyl, t-butyl, n-pentyl, 2-methyl-3-butyl, n-hexyl and the like. Alkoxy radicals are oxygen ethers formed from the previously described straight or branched chain alkyl groups. Similarly, alkenyl and alkynyl groups include straight and branched chain alkenes and alkynes having 1 to 8 carbon atoms, or any number within this range. Cycloalkyl groups include alkyl ring structures containing 3 to 8 ring carbons, preferably 5 to 7 ring carbons.

As used herein, unless otherwise noted, "aryl" shall include aromatic groups such as phenyl, naphthyl, fluorenyl, and the like.

As used herein, unless otherwise noted, "heteroaryl" shall denote a stable unsubstituted or substituted five or six membered monocyclic aromatic ring system or a stable unsubstituted or substituted nine or ten membered benzo-fused heteroaromatic ring system which consists of carbon atoms and from one to six heteroatoms (preferably, one to four heteroatoms) selected from N, O or S. Examples of suitable heteroaryl groups include, but are not limited to pyridyl, pyrazinyl, pyridazinyl, pyrimidyl, thienyl, furanyl, purinyl, imidazolyl, isoxazolyl, indazolyl, isoindolyl, pyrazolyl, pyrrolyl, thiazolyl, thiadiazolyl, diaoxazolyl, triazolyl, tetrazolyl, benzimidazolyl, benzofuranyl, benzothienyl, indolyl, quinolinyl and the like. The heteroaryl may be attached at any carbon atom which results in the creation of a stable structure.

When a particular group (e.g., aryl, heteroaryl) is substituted, that group may have one or more substituents (preferably, one to five, more preferably, one to three, most preferably, one or two substituents) independently selected from the listed substituents. Moreover, the substituent(s) may be attached at any carbon atom which results in the creation of a stable structure, except when the substituted group is pyrrolyl, indolyl, imidazolyl or triazolyl, where the substituent(s) may be attached at any carbon atom or heteroatom which results in the creation of a stable structure.

As used herein, unless otherwise noted, "aralkyl" shall mean any alkyl group substituted with an aryl group such as benzyl, phenylethyl and the like. Similarly, the term "aralkoxy" indicates an alkoxy group substituted with an aryl group (e.g., benzyloxy).

As used herein, unless otherwise noted, the term "aminoalkyl" refers to an alkyl group substituted with an amino group (i.e., -alkyl-$NH_2$). The term "alkylamino" refers to an amino group substituted with an alkyl group (i.e., NH-alkyl). The term "dialkylamino" refers to an amino group which is disubstituted with alkyl groups wherein the alkyl group can be the same or different (i.e., —N-[alkyl]$_2$). Suitable alkyl and aryl groups are as defined above.

As used herein, unless otherwise noted, the term "amido" refers to C(O)—$NH_2$. The term "amidoalkyl" refers to an alkyl group substituted with an amido group (i.e. -alkyl-C(O)$NH_2$). The term "alkylamido" refers to an amido group substituted with an alkyl group (i.e. —C(O)—NH-alkyl).

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., $C_1$-$C_8$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definition(s) elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

Under standard nomenclature used throughout this disclosure, the terminal portion of the designated side chain is described first, followed by the adjacent functionality toward the point of attachment. Thus, for example, a "phenyl$C_1$-$C_8$ alkylamido$C_1$-$C_8$alkyl" substituent refers to a group of the formula

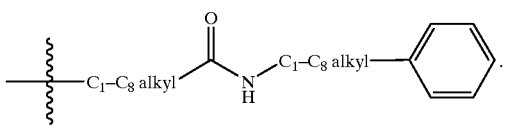

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The compounds of formula (I) and (II) that comprise this invention are generally referred to as 1,4-dithiin- and 1,4-dithiepin-1,1,4,4-tetroxide derivatives, respectively, and are synthesized via the routes outlined in Schemes 1a through 1f.

The synthesis of compounds of formula (I) and formula (II) are known to those skilled in the art and comprise the steps of:

reacting a substituted ketone with 1,2-ethanedithiol or 1,3-propanedithiol in the presence of acid catalyst such as boron trifluoride etherate, p-toluenesulfonic acid and the like, in a solvent such as dichloromethane, chloroform and the like [Afonso et al. *Synthesis*, 1991, 575] to produce the corresponding dithiolane of formula (III) and formula (IV), as illustrated in Schemes 1a and 1b,

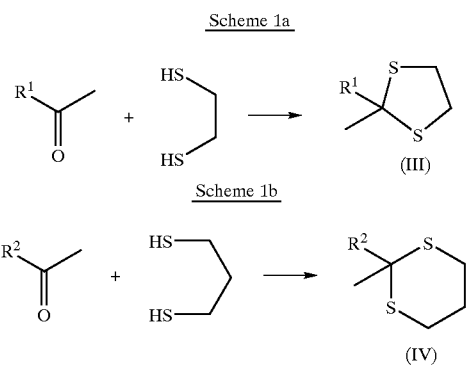

treating the dithiolane with bromine [Palumbo et al. *Synthesis*, 1991, 223], or N-bromosuccinimide/Proton Sponge® [Jaszberenyi et. al. *J. Org. Chem.*, 1991, 56, 6748] to produce the corresponding dithiin or dithiepine, respectively, as illustrated in Scheme 1c and 1d, Scheme 1c

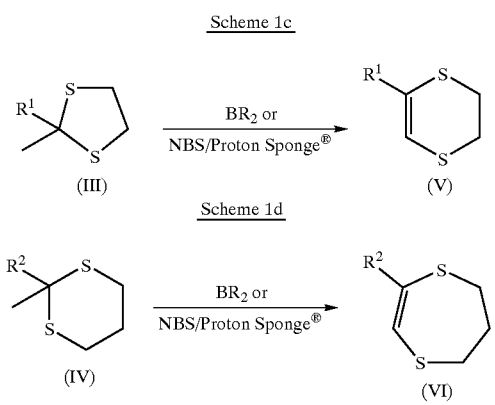

Scheme 1d treating the dithiin of formula (V) or the dithiepine of formula (VI) with an oxidizing agent such as hydrogen peroxide, 3-chloroperbenzoic acid and the like, in a solvent such as acetic acid, methylene chloride and the like, preferably acetic acid [Pollak et al. *Tetrahedron*, 1965, 1323] to afford the corresponding compounds of formula (I) and (II), as illustrated in Scheme 1e and 1f.

Scheme 1e

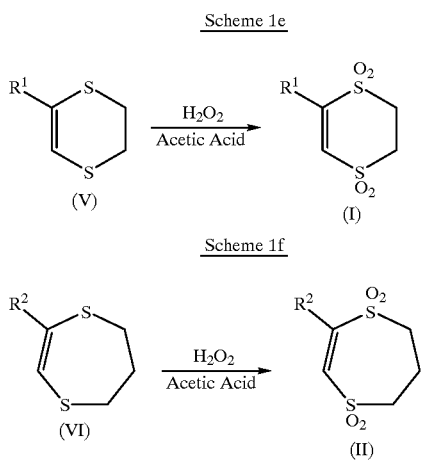

Scheme 1f

As modulators of the human galanin receptor, specifically the human galanin-1 (hGAL-1) receptor, the compounds of formula (I) and formula (II) are useful for treating feeding disorders and diseases and conditions arising therein, depression and its attending disorders, or cognitive disorders such as Alzheimer's disease or senile dementia (e.g. eating disorders, obesity, bulimia nervosa, anorexia nervosa, binge eating, diabetes, dyslipidimia, hypertension, memory loss, sleep disturbances, pain, depression, anxiety, Alzheimer's disease, senile dementia, cerebral hemorrhage, diarrhea). The compounds of formula (I) and formula (II) compete with galanin and bind to the hGAL-1. In addition, the compounds demonstrate antagonist activity by antagonizing the action of galanin at the hGAL-1 receptor—the antagonists inhibit the galanin's inhibition of cAMP formation.

The compounds described herein are ligands of the human galanin receptor, specifically the human galanin-1, human galanin-2 and human galanin-3 receptors, but are not necessarily limited solely in their pharmacological or biological action due to binding to this or any G-coupled protein.

The present invention further comprises pharmaceutical compositions containing one or more compounds of formula (I) and/or (II) with a pharmaceutically acceptable carrier.

Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50–100 mg and may be given at a dosage of from about 0.5–5.0 mg/kg/day, preferably from about 1.0–3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The present invention further provides a method of treatment of central nervous system disorders and affective conditions such as eating disorder, obesity, bulimia nervosa, anorexia nervosa, binge eating, diabetes, dyslipidimia, hypertension, memory loss, sleep disturbances, pain, depression, anxiety, Alzheimer's disease, senile dementia, cerebral hemorrhage, or diarrhea.

The utility of the compounds to treat disorders of the central nervous system as described above, can be determined according to the procedures described herein. The present invention therefore provides a method of treating central nervous system disorders in a subject in need thereof which comprises administering any of the compounds as defined herein in a quantity effective to treat central nervous system disorders. The compound may be administered to a patient by any conventional route of administration, including, but not limited to, intravenous, oral, subcutaneous, intramuscular, intradermal and parenteral.

The method of treating central nervous system disorders described in the present invention may also be carried out using a pharmaceutical composition comprising any of the compounds as defined herein and a pharmaceutically acceptable carrier. The pharmaceutical composition may contain between about 0.1 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of the central nervous system is required.

The daily dosage of the products may be varied over a wide range from 0.01 to 1,000 mg per adult human per day. For oral administration, the compositions are preferably provided in the form of tablets containing, 0.01,0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following example(s) describe the invention in greater detail and are intended to illustrate the invention, but not to limit it. All compounds were identified by a variety of methods including nuclear magnetic resonance spectroscopy, mass spectrometry and in some cases, infrared spectroscopy and elemental analysis. Nuclear magnetic resonance (300 MHz NMR) data is reported in parts per million downfield from tetramethylsilane. Mass spectra data is reported in mass/charge (m/z) units. The terms $^1$H NMR and Cl or FAB mass spec indicate that the compounds were analyzed and the results of those analyses confirmed the structure of the particular compounds. Unless otherwise noted, the materials used in the example were obtained from readily available commercial sources or synthesized by standard methods known to those skilled in the art.

Abbreviations used in the instant specification, particularly the Schemes and Examples, are as follows:

Cmpd=Compound
DMSO=Dimethyl sulfoxide
EDTA=Ethylenediaminetetraacetic Acic
HEPES=4-(2-hydroxyethyl)-1-piperazineethanesulfonic acid
MS (NH$_4^+$) Chemical ionization mass spectrometry
NBS=N-Bromosuccinimide
PPT=Precipitate
RT or rt=Room temperature

EXAMPLE 1

2,3-dihydro-2-(4-methylphenyl)-1,4-dithiepin-1,1,4,4-tetraoxide

A solution of 4'-methylacetophenone (10 g, 74.5 mmol) and dichloromethane (200 mL) was treated dropwise with boron trifluoroetherate (12.5 mL, 104 mmol) at room temperature. To the resulting solution was added 1,3-propanedithiol (7.45 mL, 74.5 mmol) and the reaction mixture was stirred for 4 h at room temperature. The reaction was quenched carefully with saturated NaHCO$_3$ solution and extracted with dichloromethane. The organic layer was separated and evaporated in vacuo. The residue was dissolved in ethyl acetate and washed with 1 N NaOH, water, and saturated NaCl solution. The organic layer was separated, dried with MgSO$_4$, filtered and solvent evaporated in vacuo to yield a crude oil. Purification of the crude oil via flash chromatography (50% CH$_2$Cl$_2$/hexane) afforded crystalline 4'-methylacetophenone propylene thioketal.

A solution of the 4'-methylacetophenone propylene thioketal (7.63 g, 34 mmol), N-bromosuccinimide (6.05 g, 34 mmol), and chloroform (75 mL) was stirred at room temperature for 20 min followed by the addition of 1,8-dimethylamino naphthalene (7.28 g, 34 mmol). The reaction was stirred for ten minutes, filtered, and the organic solvent was evaporated in vacuo. The residue was dissolved in 1:1 dichloromethane/hexane and filtered to yield a crude oil. Purification of the crude oil by flash chromatography (30% dichloromethane/hexane) yielded 2,3-dihydro-2-(4-methylphenyl)-1,4-dithiepin as an oil.

The 2,3-dihydro-2-(4-methylphenyl)-1,4-dithiin (1.86 g, 8.37 mmol) was dissolved in dichloromethane (10 mL) and slowly added into a mixture of 30% H$_2$O$_2$ (1 mL)/acetic acid (1 mL) at 100° C. and stirred at 100° C. for five minutes (dichloromethane evaporated). The reaction was cooled and stored in the freezer overnight. Crystals were collected by filtration yielding pure 2,3-dihydro-2-(4-methylphenyl)-1,4-dithiepin-1,1,4,4-tetraoxide as a crystalline solid.

$^1$H NMR (300 MHz, DMSO-d$_6$) δ7.32–7.40 (m, 3H, aromatic, vinyl), 7.23–7.32 (m, 2H, aromatic), 3.90–3.98 (t, 2H, SO$_2$CH$_2$), 3.78–3.88 (t, 2H SO$_2$CH$_2$), 2.5 (m, 2H, CH$_2$), 2.331 (s, 3H, CH$_3$)

In a similar fashion, Cmpds #1–4 were prepared by reacting with 1,2-ethanedithiol, and Cmpds #5–9 and #11–41 were prepared by reacting with 1,3 propanedithiol. Structures were supported by $^1$H NMR and Cl or FAB mass spectroscopy.

EXAMPLE 2

As a specific embodiment of an oral composition, 100 mg of the compound of Example 1 is formulated with sufficient finely divided lactose to provide a total amount of 580 to 590 mg to fill a size O hard gel capsule.

EXAMPLE 3

In Vitro Testing

Human Galanin-1 Receptor Binding Assay

This assay determines the concentration (IC$_{50}$) of a test compound which prevents 50% of galanin from binding to the hGALR-1 that is contained in membranes from human Bowes melanoma cells bound to wheat germ agglutinin conjugated Scintillation Proximity Assay (SPA) beads. The IC$_{50}$ value is obtained by measuring the effect of half log increment dilutions of the test compound in duplicate using a 96-well plate (eight-rows, 12-columns).

The SPA beads (500 mg) were dissolved in 12.5 mL of assay buffer composed of 20 mM DMSO-HEPES (pH 7.4), 0.1% bovine serum albumin, 2 mM MgCl$_2$, 2 mM CaCl$_2$, and protease inhibitors. Enough of this suspension for five plates (25 μL×5×96 wells=12000 μL) was dispensed into a 50 mL sterile Falcon tube. The amount of membranes required for five plates was then added (50 μg×5×96 wells), followed by 32.5 mL of 30% DMSO-HEPES buffer. The mixture was placed on a rotator and agitated for 0.5 hours and the non-specific binding sites on the beads were blocked by the addition of 5% [final] fetal bovine serum. Each well of the 96-well plate received 100 μL of this mixture.

To the control column (column 12) rows A and B was added 3.75 μL of a 300 μM solution of galantide in 30% DMSO-HEPES buffer, to rows C and D was added 3.75 μL of 30% DMSO-HEPES buffer and to rows E and F was added 3.75 μL of a 300 μM solution of galanin in 30% DMSO-HEPES buffer. In columns 1 through 11 were added solutions of the test compound in 30% DMSO-HEPES buffer starting at 30 μM and decreasing in concentration in half-log dilutions. A solution of radioactive $^{125}$I human galanin (46.25 μL), prepared from 25 micro Curies of $^{125}$I human galanin (2000 ci/mmol) and 500 μL of assay buffer, was added to each well. The plate was sealed with adhesive paper and incubated for 16 hr at room temperature before the quench-corrected bound radioactivity was measured in a Topcount® apparatus. For each dilution, the % inhibition of galanin binding was calculated as follows:

Total binding (T)=Mean counts/minute (cpm) in row C and D in column 12 Non-specific binding (NSB)=Mean cpm in row E and F in column 12 Total specific binding (TS)=T−NSB cpm in each well=C net cpm in each well (N)=C−NSB % inhibition=100%−N×100%/TS The $IC_{50}$ values for each compound were calculated from the non-linear regression curve of the data using Prism® graphics software.

TABLE I

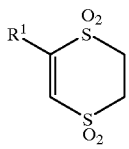

(I)

| Cmpd | R$^1$ | HGAL IC$_{50}$ | MW | MS (NH$_4^+$) |
|---|---|---|---|---|
| 1 | Phenyl | 2700 nM | 258.32 | 276 |
| 2 | 4-Bromophenyl | 1000 nM | 337.21 | 335.19 (Cl) |
| 3 | 1-amino-2-phenyl ethyl | 8000 nM | 301.39 | 302 |
| 4 | 1-[[4-n-butoxy]benz-amido]-2-phenyl ethyl | 1000 nM | 477.60 | 478.1 (Cl) |

TABLE II

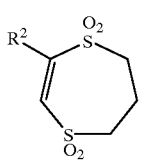

(II)

| Cmpd | R$^2$ | hGAL IC$_{50}$ | MW | MS (NH$_4^+$) |
|---|---|---|---|---|
| 5 | Phenyl | 2700 nM | 272.34 | 290 |
| 6 | 3-Methylphenyl | 1300 nM | 286.37 | 304 |
| 7 | 3-Methoxyphenyl | 910 nM | 302.37 | 320 |
| 8 | 3-Chlorophenyl | 1000 nM | 306.79 | 306 |
| 9 | 3-Bromophenyl | 890 nM | 351.24 | 370 |
| 10 | 4-Methylphenyl | 190 nM | 286.37 | 304 |
| 11 | 3-Trifluoromethylphenyl | 600 nM | 340.34 | 358 |

TABLE II-continued

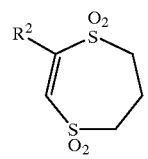

(II)

| Cmpd | R$^2$ | hGAL IC$_{50}$ | MW | MS (NH$_4^+$) |
|---|---|---|---|---|
| 12 | 2-Chlorophenyl | 640 nM | 306.79 | 324 |
| 13 | 4-Bromophenyl | 260 nM | 351.24 | 370 |
| 14 | 4-Fluorophenyl | 410 nM | 290.33 | 308 |
| 15 | 3-Methoxyphenyl | 1100 nM | 302.37 | 320 |
| 16 | 3-Fluorophenyl | 1300 nM | 290.33 | 308 |
| 17 | 4-Iodophenyl | 710 nM | 398.24 | 416 |
| 18 | 2-Methyphenyl | 1600 nM | 286.37 | 304 |
| 19 | 4-Phenoxyphenyl | 410 nM | 364.44 | 382 |
| 20 | 3-Trifluoromethoxyphenyl | 2700 nM | 356.34 | 374 |
| 21 | 4-Chlorophenyl | 1900 nM | 306.79 | 306 |
| 22 | 4-Trifluoromethylphenyl | 2100 nM | 340.34 | 358 |
| 23 | 4-Trifluoromethoxyphenyl | 490 nM | 356.34 | 374 |
| 24 | 4-biphenyl | 600 nM | 348.44 | 366 |
| 25 | 4-Cyclohexylphenyl | 1100 nM | 354.49 | 372 |
| 26 | 4-Ethylphenyl | 430 nM | 300.40 | 318 |
| 27 | 3-Iodophenyl | 850 nM | 398.24 | 398 |
| 28 | 4-Ethoxyphenyl | 590 nM | 316.40 | 334 |
| 29 | 2-Fluorophenyl | 430 nM | 290.33 | 308 |
| 30 | 2-Bromophenyl | 570 nM | 351.24 | 369 |
| 31 | 2-Trifluoromethylphenyl | 580 nM | 340.34 | 358 |
| 32 | 2-Methoxyphenyl | 1000 nM | 302.37 | 320 |
| 33 | 3-(phenyloxycarbonyl) phenyl | 440 nM | 392.45 | 410 |
| 34 | 4-(ethyloxycarbonyl) phenyl | 1000 nM | 344.41 | 362 |
| 35 | 4-(phenylsulfonyl) phenyl | 1580 nM | 412.51 | 413.2 FAB |
| 36 | 4-(propylamido) phenyl | 1039 nM | 357.45 | 358 |
| 37 | 1-naphthyl | 371 nM | 322.40 | 340 |
| 38 | 4-(phenylethylamido) phenyl | 1056 nM | 419.52 | 420 |
| 39 | 4-carboxyphenyl | | 316.35 | 334 |
| 40 | 2-thienyl | 1300 nM | 278.37 | 296 |
| 41 | 3-thienyl | 1300 nM | 278.37 | 296 |

EXAMPLE 4

In Vivo Testing

Rat Galanin-1 Receptor Mediated Inhibition of Acetylcholine Release from Rat Brain Cortical Slices and Rat Brain Synaptosomes Superfusion Procedure for Brain Slices Rat brain cerebrocortical tissues were chopped into slices of 300×300×3,000 mm using a McIlwain tissue chopper. The slices were washed and incubated at 37° C. for 30 min in Krebs-Ringer solution: NaCl 118 mM, KCl 4.8 mM, $CaCl_2$ 1.3 mM, $KH_2PO_4$ 1.2 mM, $MgSO_4$ 1.2 mM, $NaHCO_3$, 25 mM, glucose 10 uM, ascorbic acid 100 mM (previously aerated for 10 min with 95% $O_2$/5% $CO_2$ to obtain a pH of 7.4) and 0.1 μM [Methyl-$^3$H]choline chloride (85 Ci/mmol, Amersham Life Sciences, Arlington Heights, Ill.). After incubation, the slices were washed three times with ice-cold physiological solution and resuspended in 6 ml of cold solution. Equal aliquots of the tissue suspension were placed in each of 6 parallel superfusion chambers (Hugo Sachs Elektronik, March-Hugstetten, Germany). A circular piece of nylon mesh (pore size 250 um) was placed just below each chamber outlet in order to prevent the loss of tissue. The chambers were perfused against gravity with oxygenated Krebs-Ringer containing 1 mM physostigmine hemisulfate at a flow rate of 1 ml/min. At the concentration used, physostigmine had no effect on the release of total radioactivity from tissue slices. The onset of superfusion was defined as time zero ($t_0$). Starting at 30 min after $t_0$, 10 min fractions of the effluent were collected.

Release of [$^3$H]acetylcholine was induced by superfusing tissues for 30 sec with 65 mM K$^+$-Krebs-Ringer solution (made by isomolar replacement of NaCl with KCl). Four potassium pulses were given respectively at 40 min ($S_1$), 70 min ($S_2$), 100 min ($S_3$) and 130 min ($S_4$) after $t_0$. No significant deterioration in fractional release was observed during the 4 consecutive stimuli. Twenty minutes preceding $S_2$, $S_3$ or $S_4$, tissues were superfused with Krebs-Ringer solution that contained various concentrations of galanin, galanin receptor antagonist, galanin +galanin receptor antagonist or vehicle (control). To permit construction of concentration-effect curves, concentrations of agents were increased 10 fold between each stimulus.

Following perfusion, the tissue was homogenized in 1 ml ethanol and aliquots of superfusates (0.4 ml) and tissue homogenates (0.04 ml) were added to 5 ml of Scintsafe PlusTM 50% (Fisher Scientific, Pittsburgh, Pa.) and radioactivity counted by liquid scintillation spectrometry. The total $^3$H content in this procedure consisted mainly of [$^3$H]acetylcholine.

Superfusion Procedure for Brain Synaptosomes

Synaptosomes (P2 fraction) were prepared from rat brain cerebrocortex according to the methods known in the art (Gary, E. G., Whittaker, U. P., The Isolation of Nerve Endings from Brain: An Electron Microscopic Study of Cell Fragments Derived by Homogenization and Centrifugation *J. Anat.*, 1962, 96, 79–87). In brief, cortical tissues were homogenized in oxygenated 20 mM HEPES-, 0.1 mM EDTA-contained 0.32 M sucrose solution (pH 7.4) in the presence of pertussis toxin (25 mg/mg tissues). Homogenates were centrifuge at 1000×g for 10 min at 4° C. The obtained supernatants were incubated at 37° C. for 1 hour under constant shaking and 95% $O_2$/5% $CO_2$ flush. Synaptosomes were pelleted by centrifuging at 15,000×g for 30 min. The obtained synaptosomes were washed and incubated at 37° C. for 30 min in Krebs-Ringer solution and 0.1 µM [Methyl-H]choline. After incubation, the synaptosomes were diluted with three volumes of ice-cold Krebs-Ringer solution and centrifuged at 15,000×g for 15 min. Equal aliquots of the tissue suspension were placed in each of 6 parallel superfusion chambers (Hugo Sachs Elektronik, March-Hugstetten, Germany) between two circular pieces of GF/B glass fiber (Whatman, England) in order to prevent the loss of tissue. The chambers were perfused against gravity with oxygenated Krebs-Ringer containing 1 mM physostigmine hemisulfate at a flow rate of 0.5 ml/min. The onset of superfusion was defined as time zero ($t_0$). Starting at 30 min after $t_0$, 10-min fractions of the effluent were collected.

Release of [$^3$H]acetylcholine was evoked by superfusing tissues as described above. No significant deterioration in fractional release was observed during the 4 consecutive stimuli. Twenty minutes preceding $S_2$ or $S_3$, tissues were superfused with Krebs-Ringer solution that contained various concentrations of galanin, galantide or vehicle (control). Following perfusion, the tissues (on filter) and aliquots of superfusates (0.5 ml) were added to 5 ml of Scintsafe PlusTM 50% (Fisher Scientific). The radioactivity counted by liquid scintillation spectrometry.

Calculation of [$^3$H]Acetylcholine Efflux

Tritium ($^3$H) efflux into the superfusate was calculated as the fraction of tritium content in the slices or synaptosomes at the onset of the respective collection period. For calculation of the stimulated tritium overflow, the estimated basal efflux (the average of the 10 min fractions immediately before and after each stimulation) was subtracted from the total tritium efflux during the 10 min fraction which began with the 30 sec K$^+$ pulse. This difference was then used to calculate the percent of K$^+$-evoked release of acetylcholine.

In order to quantify the in vitro effect of a drug on stimulated tritium outflow, the ratio of the fraction released by a given pulse, $S_n$, to that evoked by $S_1$, was determined. Data presented below are expressed as the mean fractional tritium release ±S.E.M. Statistical differences between treatments were tested by the two-tailed Student's t test or the two factor ANOVA as appropriate. Individual differences in the dose-response curve was evaluated by the Newman-Keul multiple comparison.

TABLE III

| Acetycholine Secretion | CP# 16 (10 µM + GAL) | CP# 16 (1 µM + GAL) | CP# 17 (10 µM + GAL) | CP# 17 (1 µM + GAL) |
|---|---|---|---|---|
| Basal | 2.28 (−37%) | 2.20 (−38.9%) | 2.27 (−37%) | 2.19 (−39.2%) |
| Stimulated | 8.27 | 6.31 (−23.9%) | 6.44 (−22.3%) | 5.37 (−35.2%) |

| ACh Secretion | Control | GAL (0.1 nM) |
|---|---|---|
| Basal | 3.60 ± 0.07 | 2.30 ± 0.06 (−36.1%) |
| Stimulated | 8.29 ± 0.04 | 4.65 ± 0.21 (−44%) |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula

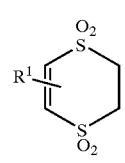

(I)

or

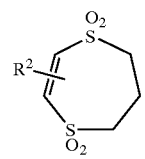

(II)

wherein $R^1$ is selected from the group consisting of substituted arC$_1$–C$_8$ alkyl where the substituent is NR$^3$R$^4$;

$R^2$ is selected from the group consisting of C$_1$–C$_8$ alkyl, unsubstituted or substituted aryl, and unsubstituted or substituted heteroaryl, where the substituents on the aryl or heteroaryl are independently selected from one or more of halogen, C$_1$–C$_8$ alkyl, C$_3$–C$_8$ cycloalkyl, C$_1$–C$_8$ alkoxy, fluorinated C$_1$–C$_8$ alkyl, fluorinated C$_1$–C$_8$ alkoxy, aryloxy, C$_1$–C$_8$ alkylamido, aryl, carboxy, C$_1$–C$_8$ alkoxycarbonyl, aryloxycarbonyl, arylsulfonyl, or arC$_1$–C$_8$ alkylamido; and $R^3$ and $R^4$ are independently selected from hydrogen, $C_1$–$C_8$ alkyl, benzoyl or substituted benzoyl where the substituent is $C_1$–$C_8$ alkoxy;

provided that when $R^2$ is poly-substituted phenyl, the substituents are independently selected from two or more of halogen, $C_1$–$C_8$ alkyl, $C_3$–$C_8$ cycloalkyl, $C_2$–$C_8$ alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or ar$C_1$–$C_8$ alkylamido;

and pharmaceutically acceptable salts thereof.

2. The compound of claim 1, of the formula

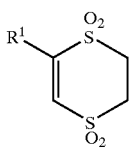

(I)

or

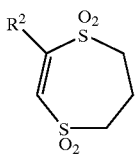

(II)

and pharmaceutically acceptable salts thereof.

3. The compound of claim 2, wherein $R^1$ is substituted phenyl$C_1$–$C_4$ alkyl where the alkyl portion of the phenyl$C_1$–$C_4$ alkyl is substituted with $NR^3R^4$;

$R^2$ is selected from the group consisting of unsubstituted or substituted aryl, and unsubstituted heteroaryl, where the substituents on the aryl are one or two substituents independently selected from halogen, $C_1$–$C_6$ alkyl, $C_5$–$C_6$ cycloalkyl, $C_1$–$C_6$ alkoxy, fluorinated $C_1$–$C_4$ alkyl, fluorinated $C_1$–$C_4$ alkoxy, phenyloxy, $C_1$–$C_6$ alkylamido, aryl, carboxy, $C_1$–$C_6$ alkoxycarbonyl, phenyloxycarbonyl, phenylsulfonyl, or ar$C_1$–$C_4$ alkylamido; and $R^3$ and $R^4$ are independently selected from hydrogen, $C_1$–$C_6$ alkyl, benzoyl or substituted benzoyl where the substituent is $C_1$–$C_6$ alkoxy;

provided that when $R^2$ is di-substituted phenyl, the substituents are independently selected from two or more of halogen, $C_1$–$C_8$ alkyl, $C_3$–$C_8$ cycloalkyl, $C_2$–$C_8$ alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or ar$C_1$–$C_8$ alkylamido;

and pharmaceutically acceptable salts thereof.

4. The compound of claim 3, wherein $R^1$ is selected from 1-amino-2-phenylethyl or 1-[[4-butoxy]benzamido]-2-phenylethyl; and $R^2$ is selected from the group consisting of thienyl, naphthyl, phenyl and mono-substituted phenyl wherein the substituent on the phenyl is selected from halogen, $C_1$–$C_6$ alkyl, $C_5$–$C_6$ cycloalkyl, $C_1$–$C_6$ alkoxy, trifluoromethyl, trifluoromethoxy, phenyloxy, $C_1$–$C_6$ alkylamido, phenyl, carboxy, $C_1$–$C_4$ alkoxycarbonyl, phenyloxycarbonyl, phenylsulfonyl, or phenyl$C_1$–$C_4$ alkylamido;

and pharmaceutically acceptable salts thereof.

5. The compound of claim 4, of the formula (II)

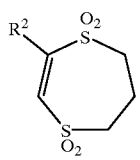

(II)

wherein $R^2$ is selected from 2-thienyl, 3-thienyl, phenyl, 1-naphthyl, or mono-substituted phenyl wherein the substituent is selected from the group consisting of 4-methyl, 4-ethyl, 4-ethoxy, 2-fluoro, 4-fluoro, 2-bromo, 4-bromo, 4-phenyl, 4-phenoxy, 2-trifluoromethyl, 3-trifluoromethyl, 4-trifluoromethoxy, and 3-phenyloxycarbonyl;

and pharmaceutically acceptable salts thereof.

6. The compound of claim 4, selected from 2,3-dihydro-2-(1-amino-2-phenylethyl)-1,4-dithiin-1,1,4,4,-tetraoxide;

2,3-dihydro-2-(1-[[4-n-butoxy]benzamido]-2-phenylethyl)-1,4-dithiin-1,1,4,4,-tetraoxide;

2,3-dihydro-2-phenyl-1,4-dithiepin-1,1,4,4-tetraoxide;

2,3-dihydro-2-(3-methylphenyl)-1,4-dithiepin-1,1,4,4-tetraoxide;

2,3-dihydro-2-(3-methoxyphenyl)-1,4-dithiepin-1,1,4,4-tetraoxide;

2,3-dihydro-2-(3-chlorophenyl)-1,4-dithiepin-1,1,4,4-tetraoxide;

2,3-dihydro-2-(3-bromophenyl)-1,4-dithiepin-1,1,4,4-tetraoxide;

2,3-dihydro-2-(4-methylphenyl)-1,4-dithiepin-1,1,4,4-tetraoxide;

2,3-dihydro-2-(3-trifluoromethylphenyl)-1,4-dithiepin-1,1,4,4-tetraoxide;

2,3-dihydro-2-(2-chlorophenyl)-1,4-dithiepin-1,1,4,4-tetraoxide;

2,3-dihydro-2-(4-bromophenyl)-1,4-dithiepin-1,1,4,4-tetraoxide;

2,3-dihydro-2-(4-fluorophenyl)-1,4-dithiepin-1,1,4,4-tetraoxide;

2,3-dihydro-2-(3-methoxyphenyl)-1,4-dithiepin-1,1,4,4-tetraoxide;

2,3-dihydro-2-(3-fluorophenyl)-1,4-dithiepin-1,1,4,4-tetraoxide;

2,3-dihydro-2-(4-iodophenyl)-1,4-dithiepin-1,1,4,4-tetraoxide;

2,3-dihydro-2-(2-methylphenyl)-1,4-dithiepin-1,1,4,4-tetraoxide;

2,3-dihydro-2-(4-phenoxyphenyl)-1,4-dithiepin-1,1,4,4-tetraoxide;

2,3-dihydro-2-(3-trifluoromethoxyphenyl)-1,4-dithiepin-1,1,4,4-tetraoxide;

2,3-dihydro-2-(4-chlorophenyl)-1,4-dithiepin-1,1,4,4-tetraoxide;

2,3-dihydro-2-(4-trifluoromethylphenyl)-1,4-dithiepin-1,1,4,4-tetraoxide;

2,3-dihydro-2-(4-trifluoromethoxyphenyl)-1,4-dithiepin-1,1,4,4-tetraoxide;

2,3-dihydro-2-(4-biphenyl)-1,4-dithiepin-1,1,4,4-tetraoxide;

2,3-dihydro-2-(4-cyclohexylphenyl)-1,4-dithiepin-1,1,4,4-tetraoxide;

2,3-dihydro-2-(4-ethylphenyl)-1,4-dithiepin-1,1,4,4-tetraoxide;

2,3-dihydro-2-(3-iodophenyl)-1,4-dithiepin-1,1,4,4-tetraoxide;
2,3-dihydro-2-(4-ethoxyphenyl)-1,4-dithiepin-1,1,4,4-tetraoxide;
2,3-dihydro-2-(2-fluorophenyl)-1,4-dithiepin-1,1,4,4-tetraoxide;
2,3-dihydro-2-(2-bromophenyl)-1,4-dithiepin-1,1,4,4-tetraoxide;
2,3-dihydro-2-(2-trifluoromethylphenyl)-1,4-dithiepin-1,1,4,4-tetraoxide;
2,3-dihydro-2-(2-methoxyphenyl)-1,4-dithiepin-1,1,4,4-tetraoxide;
2,3-dihydro-2-(3-[phenyloxycarbonyl]phenyl)-1,4-dithiepin-1,1,4,4-tetraoxide;
2,3-dihydro-2-(4-[ethoxycarbonyl]phenyl)-1,4-dithiepin-1,1,4,4-tetraoxide;
2,3-dihydro-2-(4-phenylsulfonylphenyl)-1,4-dithiepin-1,1,4,4-tetraoxide;
2,3-dihydro-2-(4-[(propylamino)carbonyl]phenyl)-1,4-dithiepin-1,1,4,4-tetraoxide;
2,3-dihydro-2-(1-naphthyl)-1,4-dithiepin-1,1,4,4-tetraoxide;
2,3-dihydro-2-(4-[(phenylethylamino)carbonyl]phenyl)-1,4-dithiepin-1,1,4,4-tetraoxide;
2,3-dihydro-2-(4-carboxyphenyl)-1,4-dithiepin-1,1,4,4-tetraoxide;
2,3-dihydro-2-(2-thienyl)-1,4-dithiepin-1,1,4,4-tetraoxide; or
2,3-dihydro-2-(3-thienyl)-1,4-dithiepin-1,1,4,4-tetraoxide;
and pharmaceutically acceptable salts thereof.

7. The compound of claim 6 selected from:
2,3-dihydro-2-(4-methylphenyl)-1,4-dithiepin-1,1,4,4-tetraoxide; or
2,3-dihydro-2-(4-bromophenyl)-1,4-dithiepin-1,1,4,4-tetraoxide
and pharmaceutically acceptable salts thereof.

8. A pharmaceutical composition comprising a compound of claim 1 and a pharmaceutically acceptable carrier.

9. A pharmaceutical composition made by mixing a compound of claim 1 and a pharmaceutically acceptable carrier.

10. A process for making a pharmaceutical composition comprising mixing a compound of claim 1 and a pharmaceutically acceptable carrier.

11. A method of treating a disorder mediated by a human galanin receptor in a subject in need thereof comprising administering to the subject a therapeutically effective amount of a compound of the formula

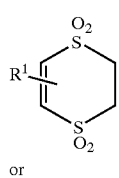

(I)

or

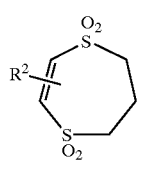

(II)

wherein
$R^1$ is selected from the group consisting of $arC_1$–$C_8$ alkyl, substituted $arC_1$–$C_8$ alkyl where the substituent is $NR^3R^4$, $C_1$–$C_8$ alkyl, unsubstituted or substituted aryl, and unsubstituted or substituted heteroaryl, where the substituents on the aryl or heteroaryl are independently selected from one or more of halogen, $C_1$–$C_8$ alkyl, $C_3$–$C_8$ cycloalkyl, $C_1$–$C$alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or $arC_1$–$C_8$ alkylamido;
$R^2$ is selected from the group consisting of $C_1$–$C_8$ alkyl, unsubstituted or substituted $arC_1$–$C_8$alkyl, unsubstituted or substituted aryl, and unsubstituted or substituted heteroaryl, where the substituents on the aryl or heteroaryl are independently selected from one or more of halogen, $C_1$–$C_8$ alkyl, $C_3$–$C_8$ cycloalkyl, $C_1$–$C_8$ alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or $arC_1$–$C_8$ alkylamido; and
$R^3$ and $R^4$ are independently selected from hydrogen, $C_1$–$C_8$ alkyl, benzoyl or substituted benzoyl where the substituent is $C_1$–$C_8$ alkoxy;
and pharmaceutically acceptable salts thereof.

12. The method of claim 11, wherein the compound has the formula

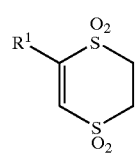

(I)

or

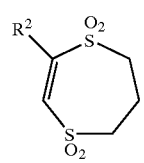

(II)

and pharmaceutically acceptable salts thereof.

13. The method of claim 12, wherein
$R^1$ is selected from the group consisting of unsubstituted phenyl$C_1$–$C_4$ alkyl, substituted phenyl$C_1$–$C_4$ alkyl where the alkyl portion of the phenyl$C_1$–$C_4$ alkyl is substituted with $NR^3R^4$, $C_1$–$C_6$ alkyl, $C_1$–$C_6$ alkoxy, unsubstituted or substituted aryl, and unsubstituted heteroaryl, where the substituents on the aryl are one or two substituents independently selected from halogen, $C_1$–$C_6$ alkyl, $C_5$–$C_6$ cycloalkyl, $C_1$–$C_6$ alkoxy, fluorinated $C_1$–$C_4$ alkyl, fluorinated $C_1$–$C_4$ alkoxy, phenyloxy, $C_1$–$C_6$ alkylamido, aryl, carboxy, $C_1$–$C_6$ alkoxycarbonyl, phenyloxycarbonyl, phenylsulfonyl, or $arC_1$–$C_4$ alkylamido;
$R^2$ is selected from the group consisting of unsubstituted or substituted aryl, and unsubstituted heteroaryl, where the substituents on the aryl are one or two substituents independently selected from halogen, $C_1$–$C_6$ alkyl, $C_5$–$C_6$ cycloalkyl, $C_1$–$C_6$ alkoxy, fluorinated $C_1$–$C_4$ alkyl, fluorinated $C_1$–$C_4$ alkoxy, phenyloxy, $C_1$–$C_6$ alkylamido, aryl, carboxy, $C_1$–$C_6$ alkoxycarbonyl, phenyloxycarbonyl, phenylsulfonyl, or $arC_1$–$C_4$ alkylamido; and
$R^3$ and $R^4$ are independently selected from hydrogen, $C_1$–$C_6$ alkyl, benzoyl or substituted benzoyl where the substituent is $C_1$–$C_6$ alkoxy;

and pharmaceutically acceptable salts thereof.

14. The method of claim 13, wherein $R^1$ is selected from 1-amino-2-phenylethyl or 1-[[4-butoxy]benzamido]-2-phenylethyl; and $R^2$ is selected from the group consisting of thienyl, naphthyl, phenyl and mono-substituted phenyl wherein the substituent on the phenyl is selected from halogen, $C_1$–$C_6$ alkyl, $C_5$–$C_6$ cycloalkyl, $C_1$–$C_6$ alkoxy, trifluoromethyl, trifluoromethoxy, phenyloxy, $C_1$–$C_6$ alkylamido, phenyl, carboxy, $C_1$–$C_4$ alkoxycarbonyl, phenyloxycarbonyl, phenylsulfonyl, or phenyl$C_1$–$C_4$ alkylamido;

and pharmaceutically acceptable salts thereof.

15. The method of claim 14, wherein the compound has the formula (II)

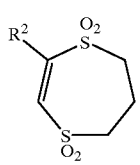

(II)

wherein $R^2$ is selected from 2-thienyl, 3-thienyl, phenyl, 1-naphthyl, or mono-substituted phenyl wherein the substituent is selected from the group consisting of 4-methyl, 4-ethyl, 4-ethoxy, 2-fluoro, 4-fluoro, 2-bromo, 4-bromo, 4-phenyl, 4-phenoxy, 2-trifluoromethyl, 3-trifluoromethyl, 4-trifluoromethoxy, and 3-phenyloxycarbonyl;

and pharmaceutically acceptable salts thereof.

16. The method of claim 11, wherein the therapeutically effective amount is between about 0.5 and about 5.0 mg/kg/day.

17. The method of claim 11, wherein the disorder is selected from an eating disorder, obesity, bulimia nervosa, anorexia nervosa, binge eating, diabetes, dyslipidimia, hypertension, memory loss, sleep disturbances, pain, depression, anxiety, Alzheimer's disease, senile dementia, cerebral hemorrhage, or diarrhea.

18. The method of claim 17, wherein the disorder is selected from obesity, depression, Alzheimer's disease or senile dementia.

19. A method of treating a disorder selected from an eating disorder, obesity, bulimia nervosa, anorexia nervosa, binge eating, diabetes, dyslipidimia, hypertension, memory loss, sleep disturbances, pain, depression, anxiety, Alzheimer's disease, senile dementia, cerebral hemorrhage, or diarrhea in a subject in need thereof, comprising administering to the subject a therapeutically effective amount of a compound of the formula

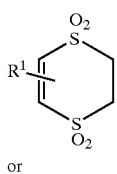

(I)

or

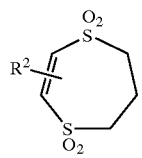

(II)

wherein $R^1$ is selected from the group consisting of ar$C_1$–$C_8$ alkyl, substituted ar$C_1$–$C_8$ alkyl where the substituent is $NR^3R^4$, $C_1$–$C_8$ alkyl, unsubstituted or substituted aryl, and unsubstituted or substituted heteroaryl, where the substituents on the aryl or heteroaryl are independently selected from one or more of halogen, $C_1$–$C_8$ alkyl, $C_3$–$C_8$ cycloalkyl, $C_1$–$C_8$ alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or ar$C_1$–$C_8$ alkylamido;

$R^2$ is selected from the group consisting of $C_1$–$C_8$ alkyl, unsubstituted or substituted ar$C_1$–$C_8$alkyl, unsubstituted or substituted aryl, and unsubstituted or substituted heteroaryl, where the substituents on the aryl or heteroaryl are independently selected from one or more of halogen, $C_1$–$C_8$ alkyl, $C_3$–$C_8$ cycloalkyl, $C_1$–$C_8$ alkoxy, fluorinated $C_1$–$C_8$ alkyl, fluorinated $C_1$–$C_8$ alkoxy, aryloxy, $C_1$–$C_8$ alkylamido, aryl, carboxy, $C_1$–$C_8$ alkoxycarbonyl, aryloxycarbonyl, arylsulfonyl, or ar$C_1$–$C_8$ alkylamido; and $R^3$ and $R^4$ are independently selected from hydrogen, $C_1$–$C_8$ alkyl, benzoyl or substituted benzoyl where the substituent is $C_1$–$C_8$ alkoxy;

and pharmaceutically acceptable salts thereof.

20. The method of claim 19, wherein the disorder is selected from obesity, depression, Alzheimer's disease or senile dementia.

21. The method of claim 19, wherein the compound has the formula

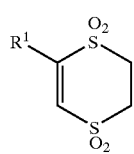

(I)

or

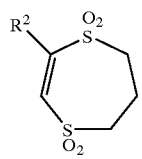

(II)

and pharmaceutically acceptable salts thereof.

22. The method of claim 21, wherein $R^1$ is selected from the group consisting of unsubstituted phenyl$C_1$–$C_4$ alkyl, substituted phenyl$C_1$–$C_4$ alkyl where the alkyl portion of the phenyl$C_1$–$C_4$ alkyl is substituted with $NR3R^4$, $C_1$–$C_8$alkyl, $C_1$–$C_6$ alkoxy, unsubstituted or substituted aryl, and unsubstituted heteroaryl, where the substituents on the aryl are one or two substituents independently selected from halogen, $C_1$–$C_6$ alkyl, $C_5$–$C_6$ cycloalkyl, $C_1$–$C_6$ alkoxy, fluorinated $C_1$–$C_4$ alkyl, fluorinated $C_1$–$C_4$ alkoxy, phenyloxy, $C_1$–$C_6$ alkylamido, aryl, carboxy, $C_1$–$C_6$ alkoxycarbonyl, phenyloxycarbonyl, phenylsulfonyl, or ar$C_1$–$C_4$ alkylamido;

$R^2$ is selected from the group consisting of unsubstituted or substituted aryl, and unsubstituted heteroaryl, where the substituents on the aryl are one or two substituents independently selected from halogen, $C_1$–$C_6$ alkyl, $C_5$–$C_6$ cycloalkyl, $C_1$–$C_6$ alkoxy, fluorinated $C_1$–$C_4$ alkyl, fluorinated $C_1$–$C_4$ alkoxy, phenyloxy, $C_1$–$C_6$ alkylamido, aryl, carboxy, $C_1$–$C_6$ alkoxycarbonyl, phenyloxycarbonyl, phenylsulfonyl, or ar$C_1$–$C_4$ alkylamido; and $R^3$ and $R^4$ are independently selected from hydrogen, $C_1$–$C_6$ alkyl, benzoyl or substituted benzoyl where the substituent is $C_1$–$C_6$ alkoxy;

and pharmaceutically acceptable salts thereof.

23. The method of claim 22, wherein $R_1$ is selected from 1-amino-2-phenylethyl or 1-[[4-butoxy]benzamido]-2-phenylethyl; and $R^2$ is selected from the group consisting of thienyl, naphthyl, phenyl and mono-substituted phenyl wherein the substituent on the phenyl is selected from halogen, $C_1$–$C_6$ alkyl, $C_5$–$C_6$, cycloalkyl, $C_1$–$C_6$, alkoxy, trifluoromethyl, trifluoromethoxy, phenyloxy, $C_1$–$C_6$ alkylamido, phenyl, carboxy, $C_1$–$C_4$ alkoxycarbonyl, phenyloxycarbonyl, phenylsulfonyl, or phenyl$C_1$–$C_4$ alkylamido;

and pharmaceutically acceptable salts thereof.

24. The method of claim 23, wherein the compound has the formula (II)

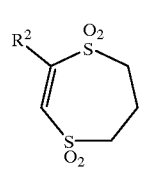

(II)

wherein $R^2$ is selected from 2-thienyl, 3-thienyl, phenyl, 1-naphthyl, or mono-substituted phenyl wherein the substituent is selected from the group consisting of 4-methyl, 4-ethyl, 4-ethoxy, 2-fluoro, 4-fluoro, 2-bromo, 4-bromo, 4-phenyl, 4-phenoxy, 2-trifluoromethyl, 3-trifluoromethyl, 4-trifluoromethoxy, and 3-phenyloxycarbonyl;

and pharmaceutically acceptable salts thereof.

25. The method of claim 19, wherein the therapeutically effective amount is between about 0.5 and about 5.0 mg/kg/day.

* * * * *